United States Patent [19]

Kopolow et al.

[11] Patent Number: 5,073,296

[45] Date of Patent: Dec. 17, 1991

[54] PREPARATION OF DISCRETE MICRODROPLETS OF AN OIL IN WATER

[75] Inventors: Stephen L. Kopolow, Plainsboro; William J. Burlant, Wayne, both of N.J.

[73] Assignee: ISP Investments Inc., Wilmington, Del.

[21] Appl. No.: 604,263

[22] Filed: Oct. 29, 1990

Related U.S. Application Data

[63] Continuation-in-part of Ser. No. 510,017, Apr. 17, 1990, abandoned.

[51] Int. Cl.⁵ .................................................. B01J 13/00
[52] U.S. Cl. ................................. 252/312; 252/308; 526/260; 526/911; 424/401
[58] Field of Search ............... 264/4.1, 4.7; 252/308, 252/316; 526/260, 911, 801; 424/63, 401

[56] References Cited

U.S. PATENT DOCUMENTS

| | | | |
|---|---|---|---|
| 2,969,330 | 1/1961 | Brynko | 252/316 |
| 3,516,941 | 7/1966 | Matson | 252/316 |
| 3,763,347 | 10/1973 | Whitaker | 219/275 |
| 4,251,386 | 2/1981 | Saeki et al. | 252/316 |
| 4,976,961 | 12/1990 | Norburg et al. | 424/401 |

*Primary Examiner*—Robert L. Stoll
*Assistant Examiner*—N. Bhat
*Attorney, Agent, or Firm*—Walter Katz; Marilyn J. Maue; Joshua J. Ward

[57] ABSTRACT

What is provided herein is a method for preparing discrete microdroplets of an oil in water stabilized by in situ polymerization of a water-soluble vinyl monomer. The method comprises dispersing the oil in water, adding the water-soluble vinyl monomer, preferably vinylpyrrolidone, optionally with a comonomer, and polymerizing the monomer or comonomers in situ such that the oil is stabilized in the resulting polymer solution as discrete microdroplets.

32 Claims, 1 Drawing Sheet

PREPARATION OF DISCRETE MICRODROPLETS OF AN OIL IN WATER

CROSS-REFERENCE TO RELATED PATENT APPLICATIONS

This application is a continuation-in-part of copending U.S. Patent application, Ser. No. 510,017, filed Apr. 17, 1990, by the same inventors, and assigned to the same assignee, as herein now abandoned.

BACKGROUND OF THE INVENTION

1. Field of the invention

This invention relates to a method for stabilization of oils in water, and more particularly, to a method for preparing stable, discrete microdroplets of an oil in water stabilized by a water-soluble polymer solution.

2. Description of the Prior Art

The unique properties of many oils make it desirable to include them in aqueous-based compositions. For example, cosmetically-active materials such as silicone oils, fluids and gums, mineral oils, and water-insoluble organic esters such as isopropropyl palmitate and isopropyl myristate, are particularly useful in cosmetic formulations for the skin and hair. In such compositions, their lubricity properties impart conditioning action for the user. However, such oils are immiscible with water which makes it very difficult to maintain a stable aqueous dispersion without rapid separation of the composition into oil and water phases. To solve the problem of providing effective dispersibility of such materials in water, it has been necessary to include a surfactant in aqueous cosmetic compositions containing cosmetically-active oils in order to maintain dispersed droplets of the oil in the aqueous solution. However, the use of surfactants increases the cost of the product and may effect the quality of the composition. In addition, even with a surfactant present, the stability of the dispersion is often not completely satisfactory.

Another approach is to form macroscopic capsules of an oil by in situ aqueous polymerization of oil soluble monomers. For example, Brynko, in U.S. Pats. 2,969,330 and 2,969,331, described the preparation of pressure-rupturable capsules of a chlorinated diphenyl oil in water by dissolving styrene, an acrylate or vinyl acetate monomer in the oil, dispersing the monomer-containing oil in water with the aid of an emulsifier to form droplets, and polymerizing the monomer to form an encapsulating wall of solid polymer material around each droplet of oil.

Berg, in *J. Microencapsulation* (1989) 6, No. 3, 327-337, also described a process for the microencapsulation of emulsified oil droplets by in situ vinyl polymerization. However, the process was limited to the use of methyl methacrylate, an oil soluble monomer, to form a polymer shell around emulsified oil droplets of decane and hexadecane.

De Luca, in U.S. 4,741,872, described the preparation of biodegradable microspheres having a three-dimensional network in which biologically active macromolecular agents were physically entrapped therein. The method involved emulsifying a vinyl derivative of a biodegradable hydrophilic polymer, a water-soluble monovinyl monomer, and a biologically active macromolecular agent, in water, and copolymerizing the vinyl compounds.

However, these and other processes have not provided a method by which cosmetically active oils, such as silicone oils, can be prepared as a stable dispersion in an aqueous medium. Nor does the prior art suggest a procedure for allowing such oils to maintain themselves in stable condition in an aqueous cosmetic formulation.

Accordingly, it is an object of the present invention to provide a process for stabilizing oils in water, preferably in the form of microdroplets, maintained discretely and for an extended period of time in an aqueous medium.

Another object of this invention is to provide a method for preparing an aqueous composition which includes stable, discrete microdroplets of an oil dispersed therein.

Still another object of the present invention is to provide a method of preparing a composition in which said microdroplets are homogeneously distributed in the composition.

Yet another object is to provide such stable, dispersed microdroplets by in situ polymerization of a water-soluble vinyl monomer, such as vinylpyrrolidone, in the presence of dispersed droplets of a water-insoluble oil, such as silicone oil, in water.

Among the other objects of the invention is to provide a cosmetic formulation containing stable, discrete microdroplets of a cosmetically-active oil stabilized in an aqueous solution in situ polymerized vinylpyrrolidone.

These and other objects and features of the invention will be made apparent from the following description thereof.

ABBREVIATIONS AND DEFINITIONS

Oil—A compound which is a water-insoluble liquid at room temperature and has an oily consistency
VO—Vinylpyrrolidone
MAPTAC—Methacrylamidopropyltrimethylammonium chloride
PVP—Polyvinylpyrrolidone
DM—Polydimethylsiloxane, Dimethicone, 100 cs, Petrarch Chem. Co; 1000 cs, Dow Corning Corp.
MO—Mineral oil
TBP—Tert-butyl peroctoate, e.g. Trigonox® 21 (AKZO Chem. Co.)
TBPP—t-Butylperoxy pivalate, e.g. Lupersol 11 (Atochem N.A.)
Cosmetically-active oil—An oil which imparts a particularly desirable property, e.g. lubricity, to a cosmetic formulation
Brookfield viscosity—Viscosity of Stabilized Oil in Water Product in cps, as measured using a RVT spindle #3@70 rpm

BRIEF DESCRIPTION OF THE DRAWING

The FIGURE is a photomicrograph under 15x magnification of an aqueous composition showing microdroplets of silicone oil stabilized in a polymer solution formed by in situ polymerization of vinylpyrrolidone monomer.

SUMMARY OF THE INVENTION

Figure 1:
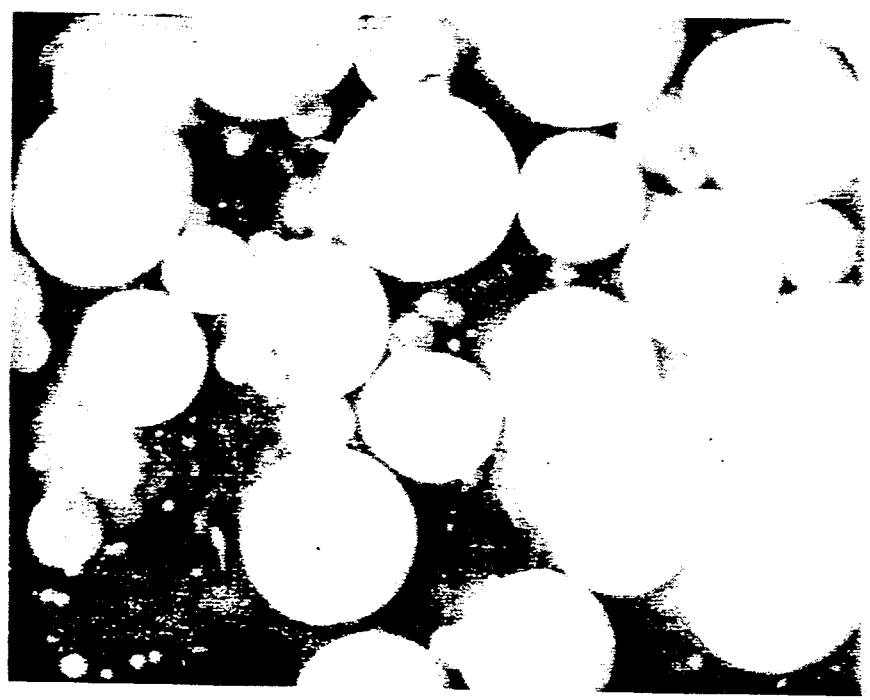

What is provided herein is a method for preparing stable, discrete microdroplets of an oil in water stabilized in a polymer solution of an in situ polymerized, water-soluble vinyl monomer. The method comprises dispersing the oil in water to form microdroplets, adding a water-soluble vinyl monomer, such as vinylpyrrolidone, optionally with a comonomer, such as methacrylamidopropylammonium chloride, and polymerizing the monomer or comonomers in situ such that the oil droplets are stabilized in the resultant aqueous polymer solution.

In the preferred form of the invention, the oil is cosmetically-active, such as is characteristic of silicone oils, mineral oils and water-insoluble esters such as isopropyl myristate and isopropyl palmitate.

DETAILED DESCRIPTION OF THE INVENTION

The active material to be dispersed in an aqueous medium are oils which are water-insoluble liquids at room temperature, and preferably, are cosmetically-active, i.e. they impart a particularly desirable property to cosmetic formulations. Such cosmetically-active oils include silicone oils, mineral oils and water-insoluble esters such as isopropyl myristate and isopropyl palmitate.

Suitable silicone oils or fluids for use in the invention may be selected from non-volatile polyalkyl siloxanes, polyaryl siloxanes, polyalkylaryl siloxanes and polyether siloxane copolymers. Such silicone oils usually are present in the composition at a level of from about 1.0% to about 18%, preferably about 2.0% to about 8.0%. Mixtures of these compounds also may be used as long as the final mixture is non-volatile and the dispersed silicone particles are insoluble in the aqueous medium. As used herein, "insoluble" requires that the oil does not substantially dissolve in water and is essentially immiscible therewith.

Non-volatile polyalkylsiloxanes include, for example, polydimethylsiloxanes (Dimethicone) with viscosities ranging from about 5–600,000 centistokes (cs) at 25° C. These siloxanes are available, for example, from the General Electric Company as the VISCASIL series and from Dow Corning as the Dow Corning 200 products. Their viscosity can be measured by the glass capillary viscometer procedure set forth in Dow Corning Corporate Test Method CTM 0004 issued July 20, 1970. Preferably, the viscosity of these siloxanes selected have a viscosity of about 100 to about 100,000 cs, and most preferably, a viscosity of up to about 15,000 cs.

Suitable non-volatile polyalkylarylsiloxanes include, for example, polymethylphenylsiloxanes having viscosities of about 15 to 65 cs at 25° C. These siloxanes are available, for example, from the General Electric as SF 1075 methylphenyl fluid or from Dow Corning as 556 Cosmetic Grade Fluid. Additionally, poly(dimethylsiloxane) (diphenylsiloxane) copolymers having a viscosity in the range of about 10 to 100,000 cs at 25° C. are useful.

These and other suitable silicones are disclosed in U.S. Pat. Nos. 2,826,551, 3,964,500 and 4,364,837; and British Patent 849,433. The disclosures of these patents are incorporated by reference herein, as is the booklet "Silicone Compounds", which was distributed by Petrarch Systems Inc. in 1984, and which describes the preparation and properties of available silicones for use in this invention.

Other suitable oils for use herein include cosmetically-active materials such as light and heavy mineral oils, and water-insoluble organic esters such as isopropyl palmitate and isopropyl myristate.

In the practice of the present invention, the oil to be dispersed is first added to water and then subjected to agitation to produce a fine dispersion of discrete oil microdroplets throughout the aqueous medium. The mixture is agitated sufficiently so that the dispersion is stable for a period of at least 5 to 10 minutes without separating into individual layers. Conventional laboratory and high speed agitators may be used for this purpose, as for example, conventional anchor or wide-span turbine agitators.

Thereafter, a water-soluble vinyl monomer, for example, a vinylpyrrolidone monomer such as vinylpyrrolidone itself or a derivative thereof such as an alkyl vinyl pyrrolidone, is added to the mixture, along with an appropriate free radical polymerization initiator. If desired, a comonomer is added for purposes of forming a copolymer. Suitable comonomers include dimethylaminopropyl methacrylate, dimethylaminoethyl methacrylate, methacrylamidopropyltrimethylammonium chloride, acrylamide and neutralized acrylic acid.

Suitable free radical polymerization initiators for polymerization of water-soluble vinyl monomers include such free radical catalysts as t-butylperoctoate, t-butylperoxy- pivalate and the like. Oil-soluble catalysts are preferred.

Thereafter, the reaction mixture is maintained at a temperature in the range of about 55° to 85° C., preferably, about 75° to 85° C., and most preferably, about 78° to 82° C., for a period of time sufficient to effect the desired polymerization and form the aqueous polymer solution necessary to stabilize the discrete microdroplets of the oil.

As the polymerization proceeds, the dispersed oil droplets become white and appear to precipitate in the aqueous medium, however, without coalescing. Generally, the observance of this white or milky color in the aqueous medium is an indication of completion of the process, which usually takes about 2 to 20 hours, preferably about 4 to 10 hours, and most preferably, about 6 to 8 hours. After completion of polymerization, the residual vinyl monomer content generally is less than about 0.1%, as measured by the iodine titration method.

The production of stable, discrete microdroplets of oil in the resulting aqueous polymer solution can be controlled by the viscosity of the aqueous polymer solution. For example, the viscosity of this medium can be increased by increasing the relative amount of vinyl monomer to oil in the original reaction mixture. By increasing the viscosity of the polymer solution, the proclivity to form a stable, homogeneous suspension of discrete microdroplets of oil throughout the entire medium is enhanced. On the other hand, reducing the viscosity of the medium by decreasing the amount of vinyl monomer in the initial mixture results in a more dilute concentration of polyvinyl polymer in the resultant mixture, which enhances the tendency to form a separate layer of discrete oil droplets.

Suitably, the ratio of monomer to oil used in the polymerization should be in the range of about 95/5 to 5/95, respectively, on a weight basis, preferably at least about 50/50. Most preferred is a range of about 90/10 to 70/30. As used herein, a "stable composition or suspension" means that the discrete oil microdroplets remain suspended in the aqueous polymer solution for at least seven days at ambient temperature.

The viscosity of the stabilized oil in water product, for example, polyvinylpyrrolidone polymer which is, obtained by in situ polymerization of vinylpyrrolidone monomer, suitably is in the range of about 3,000 to 100,000 cps, preferably about 4,000 to 60,000 cps, and most preferably, about 6,000 to 25,000 cps.

The diameter of the oil microdroplets obtained are observed to be in the range of about 0.1 to 450 microns, and usually are about 1 to 100 microns.

Referring now to the FIGURE, there is shown a photomicrograph of the composition of the invention as produced in Example 1. The photomicrograph shows microdroplets of silicone oil stabilized homogeneously throughout an aqueous polyvinylpyrrolidone solution made by in situ polymerization of vinylpyrrolidone in water.

The invention will now be described with references to the following more particular examples.

EXAMPLE 1

The in situ polymerization process of the invention was carried out in a 1-liter laboratory reactor equipped with an overhead stirring motor, a metal anchor agitator, a nitrogen gas inlet tube, a water condenser connected to a bubbler, a temperature probe connected to a temperature controller and associated with a heating mantle, and a dropping funnel.

The reactor first was purged with nitrogen and charged with 400 g. of distilled water and 10 g. of Dimethicone oil having a viscosity of 100 cs. The oil-water-then mixture was agitated vigorously at 350 rpm under nitrogen for 30 minutes whereupon the oil was dispersed as transparent, discrete microdroplets in the aqueous medium. The dispersion then was heated to 80° C. and 0.25 g. of di-tert-butylperoctoate was added. At this point, the mixture was maintained for 30 minutes with continuous stirring whereafter 90 g. of vinylpyrrolidone and an additional 0.25 g. of di-tert-butylperoctoate was added at one time while maintaining a nitrogen flow of 15 ml/min. After about 10-15 minutes, an exotherm was observed and the temperature increased to 86° C. The transparent, spherical droplets of oil became opaque. The the temperature was reduced to 80° C. and polymerization was continued for 6-8 hours with stirring. During this period, the dispersion became milky and the droplets became completely invisible. Polymerization was considered complete when the measured residual monomer content was less than 0.1%.

The composition obtained was a stable, homogeneous dispersion of microdroplets of Dimethicone oil stabilized in an aqueous polyvinylpyrrolidone solution. Upon exerting only slight pressure on the microdroplets, the silicone oil was observed to ooze out. However, the composition was quite stable for many months at room temperature, and for an extended period at the elevated temperature of 45° to 54° C.

EXAMPLES 2-3

The procedure of Example 1 was repeated using weight ratios of 80 g. of vinylpyrrolidone to 20 g. of Dimethicone oil (Example 2), and 70 g. of vinylpyrrolidone to 30 g. of Dimethicone oil (Example 3). Similar results to Example 1 were obtained in these runs.

EXAMPLE 4

The procedure of Example 1 was followed using a weight ratio of 20 g. of vinylpyrrolidone and 80 g. of Dimethicone oil. The resultant composition was not as viscous as in Example 1. The microdroplets obtained remained in discrete form, however, without coalescence, but settled to the bottom of the solution as a separate layer.

EXAMPLE 5

The procedure of Example 1 was followed using a weight ratio of 135 g. of vinylpyrrolidone to 15 g. of Dimethicone oil in 600 ml. of water. The results were substantially the same as obtained in Example 1.

EXAMPLE 6

The procedure of Example 1 was followed using a weight ratio of 135 g. of vinylpyrrolidone to 15 g. of a Dimethicone oil having a viscosity of 1,000 cs (mol. wt. of 28,000). The mixture was agitated at 700 rpm to produce a stable dispersion of the viscous silicone oil droplets in the aqueous polymer solution.

EXAMPLE 7

A pilot plant run was carried out in a 30 gal. reactor using two wide span turbine agitators having pitched and flat blades set at 200 rpm. 10,790 g. of vinylpyrrolidone, 1205 g. of Dimethicone oil, 100 cs, 48,225 g. of water, 120 g. of di-t-butylperoctoate, and 317 g. of Germaben ® preservative were used in this run. After 6 hours, polymerization was complete and a stable, homogeneous, milky aqueous dispersion of discrete, coated silicone oil droplets was obtained which dispersion remained in discrete and suspended form throughout the composition. The composition also was stable for an extended period of time.

EXAMPLE 8

The procedure of Example 1 was followed using 102 g. of vinylpyrrolidone, 11 g. of Dimethicone, 100 cs, 36 g. of a 50% aqueous solution of methacrylamidopropyltrimethylammonium chloride, 462 g. of water, 0.1 g. of tetrasodium pyrophosphate, and 0.60 g. of di-tert-butylperoctoate. A stable, homogeneous composition was obtained having a residual VP content of only 0.01%.

EXAMPLE 9

The procedure of Example 1 was followed using 90 g. of vinylpyrrolidone, 10 g. of Dimethicone oil, 100 cs, 400 g. of water and 0.75 g. of Lupersol 11. The results were similar to those obtained in Example 4.

EXAMPLE 10

The procedure of Example 1 was followed 90 g. of vinylpyrrolidone, 10 g. of light mineral oil having a density of 0.838 g/ml, 400 g. of water and 0.75 g. of Lupersol 11. The results were similar to Example 1.

EXAMPLE 11

The procedure of Example 10 was followed using 10 g. of heavy mineral oil having a density of 0.862 g/ml. The results were similar to Example 10.

CONTROL EXPERIMENTS C-1 TO C-6

Various blends of PVP polymer (K-90) and silicone oil were agitated vigorously and allowed to stand at room temperature for a day. Two layers were produced. The upper layer was a transparent, homogeneous liquid layer which contained silicone oil. The lower layer was an aqueous layer containing dissolved PVP. Discrete droplets of silicone oil were not observed in either layer. The results are presented as Examples C-1 to C-7 in Table II.

EXAMPLE 12

Film Formation

The composition of Example 1 was spread onto metal and glass substrates as films. The coated substrate was dried in vacuo at about 50° C. for about 24 hours to produce a homogeneous, thick, opaque, glassy film.

The results of these experiments are summarized in Tables I to IV below.

TABLE I

| Ex. No. | Monomer | Amt (g) | Silicone Oil | Amt (g) | Viscosity (cs) | MW | Co-monomer | Amt (g) | Medium | Amt (g) | Initiator | Amt (g) | Agitation (rpm) |
|---|---|---|---|---|---|---|---|---|---|---|---|---|---|
| 1 | VP | 90 | DM | 10 | 100 | 5970 | — | — | Water | 400 | TBP | 0.75 | 350 |
| 2 | VP | 80 | DM | 20 | 100 | 5970 | — | — | Water | 400 | TBP | 0.75 | 350 |
| 3 | VP | 70 | DM | 30 | 100 | 5970 | — | — | Water | 400 | TBP | 0.75 | 350 |
| 4 | VP | 20 | DM | 80 | 100 | 5970 | — | — | Water | 400 | TBP | 0.75 | 350 |
| 5 | VP | 135 | DM | 15 | 100 | 5970 | — | — | Water | 600 | TBP | 0.76 | 350 |
| 6 | VP | 135 | DM | 15 | 1000 | 28,000 | — | — | Water | 600 | TBP | 0.76 | 700 |
| 7* | VP | 10,790 | DM | 1205 | 100 | 5970 | — | — | Water | 48,225 | TBP | 120 | 200 |
| 8 | VP | 102 | DM | 11 | 100 | 5970 | MAPTAC | 18 | Water | 462 | TBP | 0.60 | 350 |
| 9 | VP | 90 | DM | 10 | 100 | 5970 | — | — | Water | 400 | TBPP | 0.75 | 350 |
| 10 | VP | 90 | MO | 10 | | | — | — | Water | 400 | TBP | 0.75 | 350 |
| 11 | VP | 90 | MO | 10 | | | — | — | Water | 400 | TBP | 0.75 | 350 |

*Pilot plant run

TABLE II

| Ex. No. | Polymer | % | (lb) | Silicone Oil | % | (lb) | Viscosity (cs) | M.W. | Medium | Amt (lb) | Agitation (rpm) |
|---|---|---|---|---|---|---|---|---|---|---|---|
| C-1 | PVP | 90 | 24.34 | DM | 10 | 2.76 | 100 | 5970 | Water | 110.90 | 220 |
| C-2 | PVP | 80 | 21.52 | DM | 20 | 5.38 | 100 | — | Water | 106.91 | 220 |
| C-3 | PVP | 70 | 18.83 | DM | 30 | 8.07 | 100 | — | Water | 106.91 | 220 |
| C-4 | PVP | 80 | 21.49 | DM | 20 | 5.37 | 1000 | 28,000 | Water | 106.82 | 220 |
| C-5 | PVP | 70 | 21.49 | DM | 30 | 5.37 | 1000 | 28,000 | Water | 106.82 | 220 |
| C-6 | PVP | 80 | 21.49 | DM | 20 | 5.37 | 12,500 | 67,700 | Water | 106.82 | 220 |
| C-7 | PVP | 70 | 21.49 | DM | 30 | 5.37 | 12,500 | 67,700 | Water | 106.82 | 220 |

TABLE III

| Ex. No. | % Solids | Brookfield Viscosity (cps) | Diameter of Microspheres (microns) Mean | Diameter of Microspheres (microns) Range | Form of Composition |
|---|---|---|---|---|---|
| 1 | 19.7 | 7,200 | — | — | stable, homogeneous, milky dispersion of discrete microspherical droplets of silicone oil coated by polyvinyl-pyrrolidone polymer |
| 2 | 22.0 | 24,400 | | 1–14 | |
| 3 | 21.1 | 17,300 | | 1–17 | |
| 4 | 20.0 | — | — | | |
| 5 | | | | | |
| 6 | 20.6 | 10,200 | 56 | | |
| 7 | 20.2 | 8,900 | 80 | 3–54 | |
| 8 | 30.3 | 11,300 | — | — | |
| 9 | 20.2 | 7,200 | — | — | |
| 10 | 20.45 | 4,770 | — | 0.4–13 | as in Ex. 1 |
| 11 | 21.00 | 3,180 | — | 0.5–29 | as in Ex. 1 |

TABLE IV

| Ex. No. | Brookfield Viscosity (cps) | | Range of Diameters of Microspheres (microns) |
|---|---|---|---|
| C-1 | 8,600 | 9 | 2–45 |
| C-2 | 7,970 | 8 | 3–76 |
| C-3 | 5,310 | 7 | 3–55 |
| C-4 | 5,960 | 7 | 3–109 |
| C-5 | 9,140 | 8 | 3–174 |
| C-6 | 9,860 | 8 | 5–43 |
| C-7 | 6,152 | 7 | 3–77 |

The compositions of the invention find particular use in the cosmetic industry, including cosmetic formulations for personal care products such as hair and skin care. In these products, the lubricity imparted by the oil and the film-forming characteristics of polyvinylpyrrolidone are advantageous properties for the user.

While the invention has been described with particular reference to certain embodiments thereof, it will be understood that changes and modifications may be made which are within the skill of the art. Accordingly, it is intended to be bound only by the following claims.

What is claimed is:

1. A method for stabilizing an oil in water which comprises dispersing the oil in water as microdroplets, adding a water-soluble vinyl monomer and a free radical polymerization initiator thereto, and in situ polymerizing said monomer whereby the oil microdroplets are stabilized in the resulting polymer solution.

2. A method according to claim 1 wherein said water-soluble vinyl monomer is vinylpyrrolidone.

3. A method according to claim 1 wherein a water-soluble comonomer is included in the polymerization mixture.

4. A method according to claim 3 wherein said comonomer is methacrylamidopropyltrimethylammonium chloride.

5. A method according to claim 1 wherein said stabilized microdroplets are homogeneously distributed throughout the polymer solution.

6. A method according to claim 1 wherein said oil is a cosmetically-active material.

7. A method according to claim 1 wherein said oil is a silicone having a viscosity between about 5 to 600,000 cs.

8. A method according to claim 7 wherein said silicone has a viscosity between about 100 and 100,000 cs.

9. A method according to claim 2 wherein the weight ratio of the vinylpyrrolidone monomer to oil in the polymerization mixture is about 95:5 to 5:95, respectively, on a weight basis.

10. A method according to claim 9 wherein said weight ratio is about 90:10 to about 50:50.

11. A method according to claim 1 wherein said in situ polymerization is carried out at a temperature of about 55° to about 85° C.

12. A method according to claim 2 wherein the Brookfield viscosity of the stabilized oil in water product obtained upon in situ polymerization is about 3,000 to 100,000 cps.

13. A method according to claim 1 wherein the particle sizes of the stabilized, discrete microdroplets of oil are in the range of about 0.1 to 450 microns in diameter.

14. A method according to claim 1 wherein the free radical polymerization initiator is oil soluble.

15. A method according to claim 14 wherein said initiator is t-butylperoctoate or t-butylperoxypivalate.

16. A method according to claim 6 wherein said oil is a mineral oil or a water-insoluble organic ester.

17. A method according to claim 16 wherein said ester is selected from isopropylmyristate and isopropylpalmitate.

18. A method according to claim 10 wherein said ratio is about 90:10 to about 70:30.

19. A method according to claim 13 wherein said diameter of said particles is about 1 to 100 microns, and said Brookfield viscosity of the stabilized oil in water product is about 4,000 to 60,000 cps.

20. A method according to claim 19 wherein said Brookfield viscosity is about 6,000 to 25,000 cps.

21. A method according to claim 1 wherein in situ polymerization is carried out under vigorous agitation of the polymerization mixture until a milky suspension is obtained and the residual monomer content of the product is less than about 0.5%.

22. A method according to claim 5 wherein said silicone is a non-volatile polyalkyl siloxane, a polyaryl siloxane, a polyalkylaryl siloxane or a polyether siloxane.

23. A method according to claim 22 wherein said silicone oil is a polydimethyl siloxane.

24. A method according to claim 1 wherein the discrete microdroplets of oil obtained are pressure-rupturable.

25. A method of forming a coating of the product of claim 1 on a substrate which comprises applying the product to the substrate in the form of a film.

26. A composition comprising discrete microdroplets of an oil stabilized in an aqueous polymer solution of an in situ polymerized water-soluble vinyl monomer.

27. A composition according to claim 26 wherein said monomer is vinylpyrrolidone.

28. A composition according to claim 26 wherein said oil is a cosmetically-active material.

29. A composition according to claim 28 wherein said cosmetically-active oil is a silicone, a mineral oil or a water-insoluble organic ester.

30. A composition according to claim 26 wherein said silicone oil has a viscosity of about 5 to 600,000 cs, the stabilized oil in water product has a Brookfield viscosity of about 4,000 to 60,000 cps, and the particle size of the microdroplets of silicone oil is about 0.1 to 450 microns in diameter.

31. A composition according to claim 26 wherein said silicone is a non-volatile polyalkyl siloxane, a polyaryl siloxane, a polyalkylaryl siloxane or a polyether siloxane.

32. A composition according to claim 31 wherein said silicone is a polydimethyl siloxane.

* * * * *